United States Patent
Braun et al.

(10) Patent No.: US 8,110,968 B2
(45) Date of Patent: Feb. 7, 2012

(54) IRRADIATION DEVICE WITH FILTER DISKS AND MEDIUM ENCLOSED THEREBETWEEN

(75) Inventors: Werner Braun, Wilen-Sarnen (CH); Dietmar Loffler, Ehrenkirchen (DE)

(73) Assignee: Maxs AG, Sachseln (CH)

( * ) Notice: Subject to any disclaimer, the term of this patent is extended or adjusted under 35 U.S.C. 154(b) by 620 days.

(21) Appl. No.: 12/093,928

(22) PCT Filed: Nov. 7, 2006

(86) PCT No.: PCT/EP2006/010662
§ 371 (c)(1),
(2), (4) Date: Mar. 28, 2009

(87) PCT Pub. No.: WO2007/057110
PCT Pub. Date: May 24, 2007

(65) Prior Publication Data
US 2009/0295263 A1    Dec. 3, 2009

(30) Foreign Application Priority Data
Nov. 16, 2005   (DE) .................... 20 2005 017 895 U

(51) Int. Cl.
| | |
|---|---|
| H01J 61/40 | (2006.01) |
| H01J 7/26 | (2006.01) |
| H01K 1/26 | (2006.01) |
| H01K 1/58 | (2006.01) |
| G02B 5/24 | (2006.01) |
| F21V 9/12 | (2006.01) |
| A61B 18/18 | (2006.01) |
| A61N 5/06 | (2006.01) |

(52) U.S. Cl. ............ 313/112; 313/35; 313/46; 359/886; 359/892; 362/318; 606/9; 607/90

(58) Field of Classification Search .................... 313/35, 313/46, 112; 359/886, 892; 362/318; 606/9; 607/88, 90
See application file for complete search history.

(56) References Cited

U.S. PATENT DOCUMENTS
4,388,678 A * 6/1983 Turner .......................... 362/293
(Continued)

FOREIGN PATENT DOCUMENTS
DE           911 525 C      5/1954
(Continued)

OTHER PUBLICATIONS
International Search Report for PCT/EP2006/010662, mailed Jun. 3, 2007.

*Primary Examiner* — Nimeshkumar Patel
*Assistant Examiner* — Steve Horikoshi
(74) *Attorney, Agent, or Firm* — Hultquist, PLLC; Steven J. Hultquist; Kelly K. Reynolds

(57) ABSTRACT

The present invention relates to an irradiation device having a radiation source and a filter which is arranged in the optical path and has two transparent filter disks which are substantially arranged in parallel with each other and which are held with their surrounding edges in a frame made of a material of good heat conduction, the filter disks and the frame defining a closed cavity which has provided therein a medium which selectively influences the radiation spectrum. In order to improve an irradiation device such that a degassing of the medium is prevented during heating and the filter disks do not deform as the pressure increases, provision is made for the cavity to be in the form of a pressure chamber, so that during operation of the irradiation device overpressure prevails in the cavity, and for the filter disks to be made of glass ceramic or mineral glass, wherein the filter disk which is arranged closer to the radiation source is in the form of a safety device such that it is more susceptible to breaking than the filter disk which is further away from the radiation source.

16 Claims, 3 Drawing Sheets

U.S. PATENT DOCUMENTS

Figure 1:
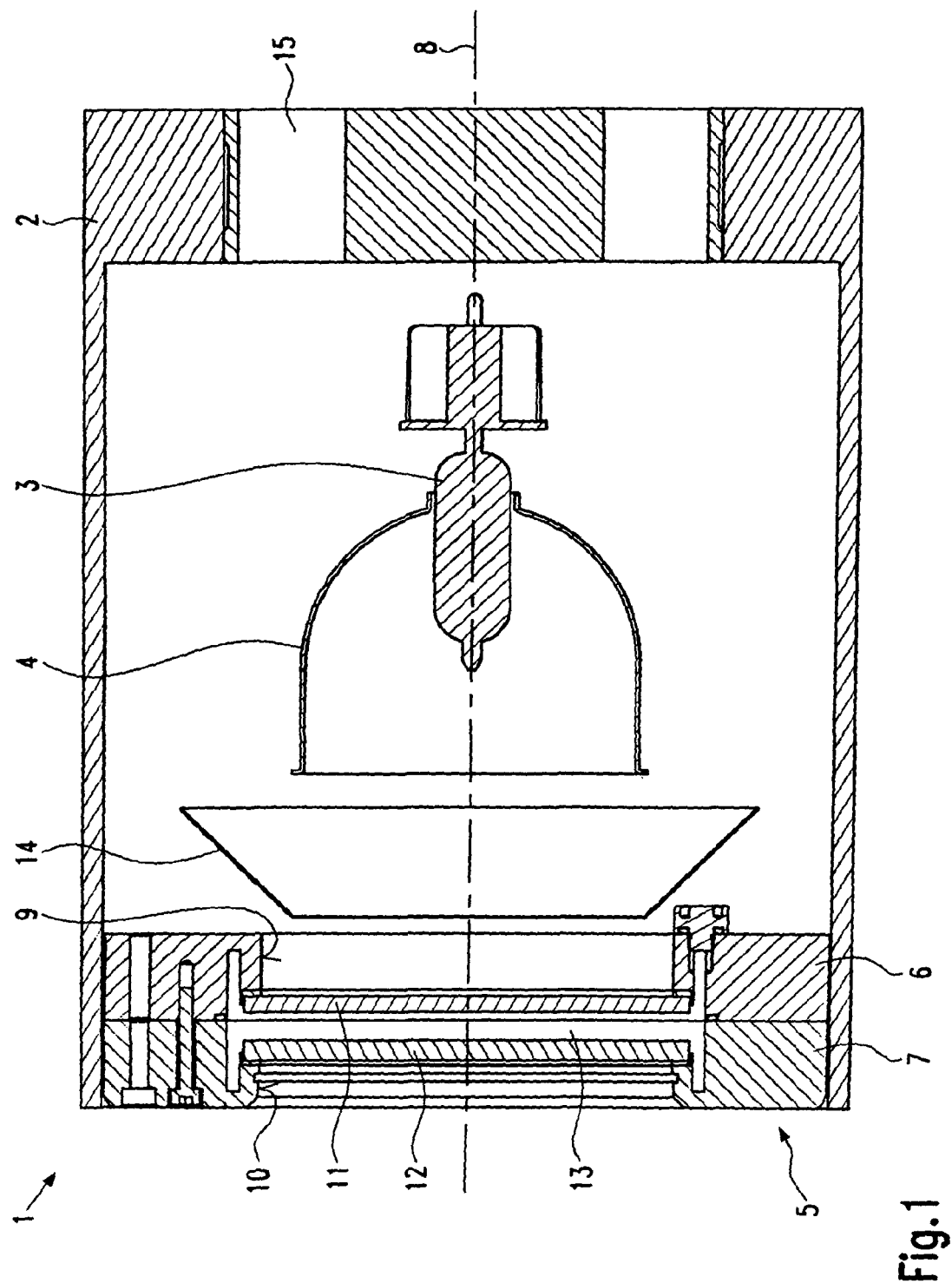

| | | | | |
|---|---|---|---|---|
| 4,939,374 A | * | 7/1990 | Greutert | 250/504 R |
| 5,337,727 A | * | 8/1994 | Borens et al. | 126/200 |
| 5,425,754 A | * | 6/1995 | Braun et al. | 607/88 |
| 5,864,419 A | * | 1/1999 | Lynam | 359/265 |
| 5,898,530 A | * | 4/1999 | Braun | 359/886 |
| 2005/0057830 A1 | * | 3/2005 | Coburn et al. | 359/885 |

FOREIGN PATENT DOCUMENTS

| | | |
|---|---|---|
| DE | 40 42 259 C1 | 6/1992 |
| DE | 195 15 182 A1 | 11/1996 |
| EP | 0 485 864 A | 5/1992 |
| EP | 0 678 705 A | 10/1995 |
| GB | 1 084 335 A | 6/1964 |

* cited by examiner

IRRADIATION DEVICE WITH FILTER DISKS AND MEDIUM ENCLOSED THEREBETWEEN

This application is a 35 U.S.C. §371 national phase application of PCT Application Ser. No. PCT/EP2006/010662, filed Nov. 7, 2006, which claims priority to European Application No. 202005017895.0, filed Nov. 16, 2005, the entire contents of which are incorporated by reference herein.

The present invention relates to an irradiation device having a radiation source and a filter which is arranged in the optical path and has two transparent filter disks which are substantially arranged in plane-parallel configuration to each other and which are held with their surrounding edges in a frame made of a material of good heat conduction, the filter disks and the frame defining a closed cavity which has provided therein a medium which selectively influences the radiation spectrum.

Such irradiation devices that can be used for heat therapy of the human body have been known for a long time. For instance, EP 0 678 705 B1 also describes an irradiation device with a radiation source and a filter arranged in the optical path. Since it is not the whole radiation spectrum emitted by the radiation source that is suited for heat therapy, a suitable filter is chosen for filtering specific bands out of the radiation spectrum. The filter consists of a frame in which two filter disks are arranged. The filter disks and the frame form a cavity that has provided therein a medium for selectively influencing the radiation spectrum. During operation of the irradiation device, the filter disks and the medium enclosed in the cavity are heated by the heat produced by the radiation source. Due to heating the medium inside the cavity expands, thereby exerting pressure on the filter disks. Since at least one of the filter disks is normally made of a plastic material, said disk can deform, whereby the filter properties would be influenced. Therefore, the irradiation device comprises a pressure compensating device which compensates for pressure variations inside the cavity. While the medium is being heated in the cavity between the filter disks, it may also happen that gases dissolved in the medium are degassing and gas bubbles have an impact on the filtering action of the filter.

It is therefore the object of the present invention to improve an irradiation device of the above-mentioned type in such a manner that a degassing of the medium is prevented during heating and the filter disks do not deform as the pressure increases.

To this end it is intended according to the invention that the cavity is configured in the form of a pressure chamber so that during operation of the irradiation device overpressure prevails in the cavity and the filter disks are made of glass ceramic or mineral glass, wherein the filter disk which is arranged closer to the radiation source is in the form of a safety device such that it is more susceptible to breaking than the filter disk which is further away from the radiation source. Due to the pressure build-up in the cavity between the filter disks a degassing of the liquid as the temperature is increasing can thereby be counteracted. Thanks to the use of materials, such as glass ceramic or mineral glass, it can be avoided that the filter disks get deformed by the pressure prevailing in the cavity, whereby a lens effect would be created that influences the filter properties. Thanks to the inventive configuration of the filter disks it is ensured that in the case of an inadmissible increase in pressure in the cavity between the filter disks the inner filter disk arranged closer to the radiation source will first break, whereby an endangerment of the patient is ruled out.

Although British patent GB 1,084,355 already discloses an illumination device which comprises a front cover consisting of two spaced-apart glass plates, the cavity in the front cover is connected to a reflector shield of the illumination device which is also provided with a cavity. Water is filled under pressure into said cavities, with the water circulating continuously to cool the illumination device. This invention, however, does not disclose that specific bands can be filtered out of the radiation spectrum of the radiation source with the help of a suitable medium, nor does it describe a safety device for the case of an inadmissible pressure build-up in the cavities.

In a further advantageous embodiment of the present invention it is described that the filter disk arranged closer to the radiation source has a predetermined breaking point. It is thereby ensured that the inner filter disk facing away from the patient will break first in the event of an inadmissible increase in pressure in the cavity. Hence, this can prevent injury of the patient.

According to a further variant the filter disk arranged closer to the radiation source is thinner than the filter disk located further away from the radiation source. This variant also ensures that the inner filter disk will break first if the pressure prevailing inside the cavity between the filter disks is inadmissibly rising. Moreover, this variant does not require any additional processing steps of the inner filter plate.

According to a further variant the filter disk arranged closer to the radiation source is made of a material more susceptible to breaking than the filter disk located further away from the radiation source. This has also the consequence that when the pressure rises in the cavity between the filter disks the inner filter disk will break first. In addition, different optical properties can be imparted to the two filter disks due to the different materials.

According to a further embodiment the frame of the irradiation device comprises cooling ribs on its outer circumference. Thanks to the cooling ribs the heat created during operation of the irradiation device is discharged, so that the medium positioned inside the cavity between the filter disks is heated to a lesser degree and thus also tends to degas to a lesser degree.

Advantageously, the irradiation device may comprise a fan and the cooling ribs may be configured such that the free cross-section between the cooling ribs and a housing of the irradiation device is optimized with respect to the air capacity of the fan. This has the effect that the air flow conveyed by the fan is not accelerated during passage through the free cross-section between the cooling ribs. This optimizes the cooling of the filter device. The development of noise is reduced in addition.

Figure 2:
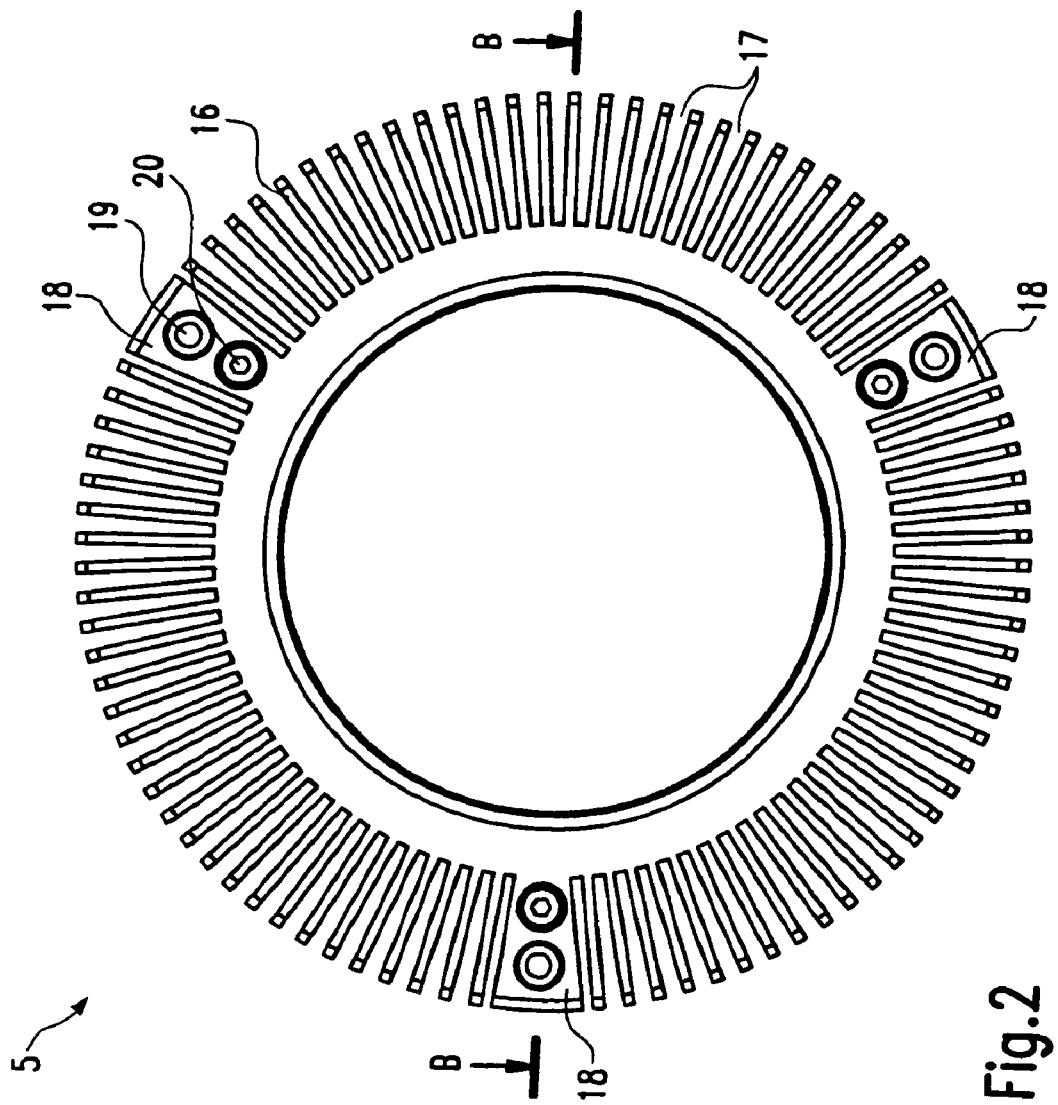
Figure 3:
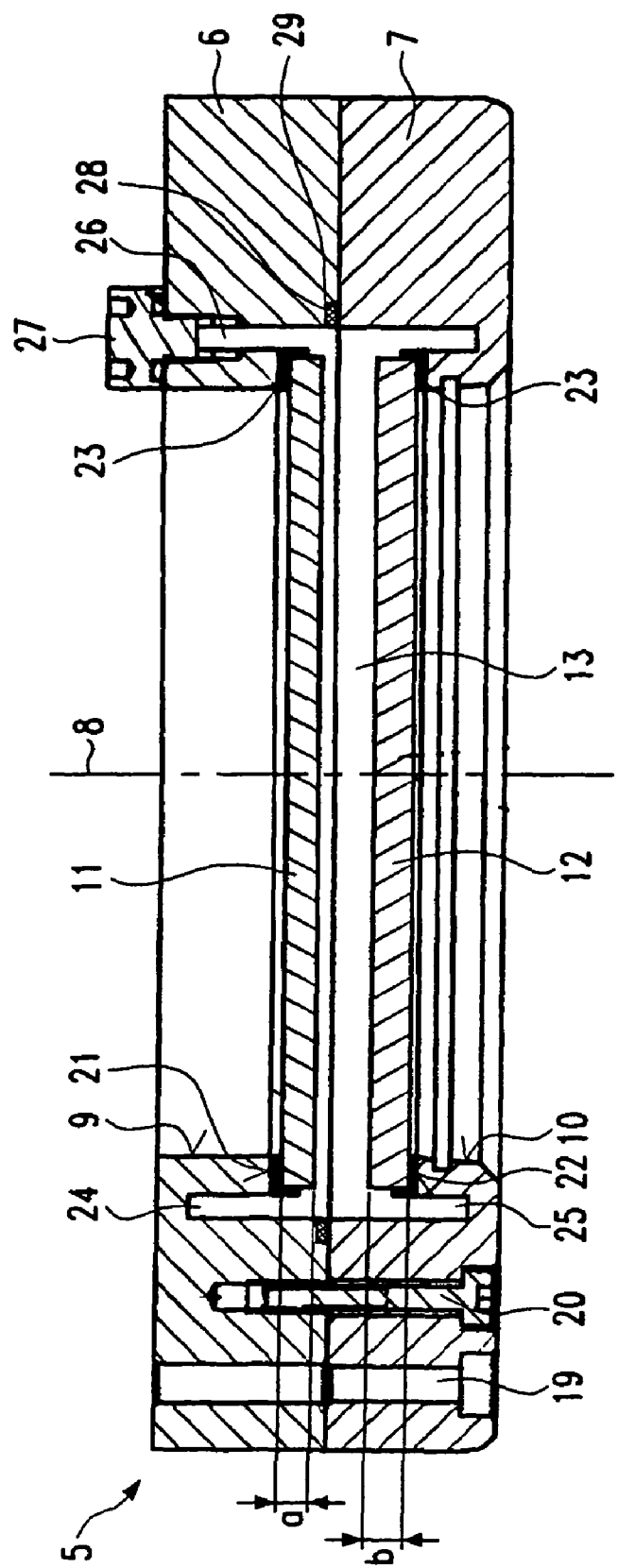

An embodiment of the present invention will now be explained in more detail with reference to a drawing, in which:

FIG. 1 is a section through an irradiation device;
FIG. 2 is a top view on the filter element with frame; and
FIG. 3 is a section through the filter element with frame along line B-B in FIG. 2.

FIG. 1 shows a section through the irradiation device 1. The irradiation device comprises a housing 2 in which a radiation source 3 is arranged. A halogen lamp may e.g. be used as the radiation source. Next to the radiation source 3 a reflector 4 is arranged. Preferably, a semispherical reflector is used with which a very homogeneous irradiation field can be accomplished. The filter element 5 is arranged in the optical path of the radiation source 3. The filter element 5 comprises a frame which consists of a frame member 6 arranged closer to the radiation source and of a frame member 7 positioned further away from the radiation source. The two frame members 6, 7 are each provided with a relatively large bore 9, 10 which is concentric to the filter axis 8. Each of the bores 9, 10 has arranged therein a filter disk 11, 12. The filter disks 11, 12 are mounted in the respective frame members 6, 7 at an axial distance relative to each other, so that a disk-shaped cavity 13 is created between them. The cavity 13 is filled with a medium that selectively influences the radiation spectrum so as to filter specific bands out of the radiation emitted by the radiation source 3. Normally, in filters used for heat therapy this medium consists of water which has fungicides possibly added to it.

A heat shield 14 which is concentric to the filter axis 8 is arranged between the radiation source 3 and the filter element 5. This heat shield 14 protects the filter element 5 against radiation that would otherwise impinge on the filter element 5 and heat up said element in addition.

A fan 15 is arranged as a further cooling device at the side of the radiation source 3 opposite the filter element.

FIG. 2 is a top view on the filter element 5 of the irradiation device 1. The two frame halves 6, 7 of the filter element 5 are provided on their edges with lamellar cooling ribs 16. The cooling ribs 16 are configured such that the free cross-section 17 created between them is optimized with respect to the ventilating capacity of the fan 15. The air flow conveyed by the fan 15 can thus flow through the free cross-section 17 formed between the cooling ribs 16 without being accelerated in this process. Thus noise is prevented and the filter element 5 is cooled in an optimum way.

Instead of cooling ribs, broadened webs 18 are arranged at regular intervals in the two frame members 6 and 7. Said webs 18 have provided therein longitudinal bores 19, 20 extending in parallel with the filter axis 8, said bores being adapted to accommodate fastening means for clamping the frame members 6 and 7 relative to each other, as well as fastening means for fastening the filter element 5 in the housing 2 of the irradiation device 1.

FIG. 3 shows a section through the filter element 5 shown in FIG. 2 along line B-B. The two frame halves 6, 7 have an enlarged web 18 with longitudinal bores 19, 20 in which fastening means may be provided so as to clamp the frame halves 6, 7 relative to each other and to fasten them in the housing 2 of the irradiation device 1. Next to the large through-bores 9, 10 arranged to be concentric to filter axis 8, a step 21, 22 is mounted in each of the frame halves 6, 7. The filter disks 11, 12 are arranged in the frame halves 6, 7 in such a way that their surrounding edges rest on the steps 21, 22. The filter disks 11, 12 can for instance be fastened in the frame halves 6, 7 with an adhesive 23. The filter disk 11 arranged closer to the radiation source 3 is configured as a safety device. In the case of an inadmissible pressure rise in the cavity 13, which is e.g. due to failure of the fan 15, the filter disk 11 is thus destroyed first. The filter disk 12 facing the patient remains intact so as to avoid injuries. To this end the thickness a of the filter disk 11 is smaller than the thickness b of the filter disk 12. It is also possible that the filter disk 11 comprises a predetermined breaking point or consists of a material less resistant to pressure than the filter disk 12. Glass ceramic or borosilicate glass may be used as the material for the filter disks 11, 12. Next to step 21, 22, each frame member 6, 7 comprises an annular groove 24, 25. Said annular grooves 24, 25 communicate with the cavity 13 between the filter disks 11 and 12 and enlarge said cavity. One of said annular grooves 24, 25 has a bore 26 through which the medium can be introduced into the cavity. The bore 26 can be closed with a suitable plug 27.

Next to the annular groove 24, 25 a further annular groove 28 is arranged in one of the frame members 6, 7. Said annular groove 28 has provided therein a sealant 29, such as an O-ring, for sealing the two frame members relative to each other.

During operation of the irradiation device 1 the radiation source 3 emits radiation which is guided via the reflector 5 towards the filter element 6 arranged in the optical path. The medium inside the cavity 13 is heated by the heat generated thereby and expands, whereby the pressure rises in the cavity 13. To avoid deformation of the filter disks 11, 12 and the lens action of the filter disks created thereby, the filter disks 11, 12 are preferably made of a rigid material, such as glass ceramic or borosilicate glass. The increased pressure prevents or reduces a degassing of the medium inside the cavity 13. Hence, no gas bubbles are formed inside the cavity 13 that might affect the filter action.

If the pressure prevailing in the cavity 13 exceeds a critical value e.g. because of a defective fan 15, the thinner filter disk 11 facing the radiation source 3 will break because said disk is more susceptible to breaking on account of its design than the filter disk 12 which is further away from the radiation source 3. This prevents, for instance, a situation where, despite of the high pressure desired during operation and in the event of a problem, pieces of broken glass impinge on the patient or are flying around otherwise in an uncontrolled way. Rather, they remain in the housing 2 of the irradiation device 1.

The invention claimed is:

1. An irradiation device (1) having a radiation source (3) and a filter (5) which is arranged in the optical path and has two transparent filter disks (11, 12) which are substantially arranged in plane-parallel configuration relative to each other and which are held with their surrounding edges in a frame (6, 7) made of a material of good heat conduction, the filter disks (11, 12) and the frame (6, 7) defining a closed cavity (13) which has provided therein a medium which selectively influences the radiation spectrum, characterized in that the cavity (13) is configured in the form of a pressure chamber so that during operation of the irradiation device (1) overpressure prevails in the cavity (13) and the filter disks (11, 12) are made of glass ceramic or mineral glass, wherein the filter disk (11) which is arranged closer to the radiation source (3) is in the form of a safety device such that it is more susceptible to breaking than the filter disk (12) which is further away from the radiation source.

2. The irradiation device (1) according to claim 1, characterized in that the filter disk (11) arranged closer to the irradiation source (3) has a predetermined breaking point.

3. The irradiation device (1) according to claim 1, characterized in that the filter disk (11) arranged closer to the irradiation source (3) is thinner than the filter disk (12) located further away from the radiation source (3).

4. The irradiation device (1) according to claim 1, characterized in that the filter disk (11) arranged closer to the irradiation source (3) is made of a material more susceptible to breaking than the filter disk (12) located further away from the radiation source (3).

5. The irradiation device (1) according to claim 1, characterized in that the frame (6, 7) comprises cooling ribs (16) on its outer circumference.

6. The irradiation device according to claim 1, characterized in that the irradiation device (1) comprises a fan (15) and the cooling ribs (16) are configured such that the free cross-section (17) between the cooling ribs (16) and a housing (2) of the irradiation device (1) is optimized with respect to the air capacity of the fan (15).

7. The irradiation device (1) according to claim 2, characterized in that the filter disk (11) arranged closer to the irradiation source (3) is thinner than the filter disk (12) located further away from the radiation source (3).

8. The irradiation device (1) according to claim 2, characterized in that the filter disk (11) arranged closer to the irradiation source (3) is made of a material more susceptible to breaking than the filter disk (12) located further away from the radiation source (3).

9. The irradiation device (1) according to claim 3, characterized in that the filter disk (11) arranged closer to the irradiation source (3) is made of a material more susceptible to breaking than the filter disk (12) located further away from the radiation source (3).

10. The irradiation device (1) according to claim 2, characterized in that the frame (6, 7) comprises cooling ribs (16) on its outer circumference.

11. The irradiation device (1) according to claim 3, characterized in that the frame (6, 7) comprises cooling ribs (16) on its outer circumference.

12. The irradiation device (1) according to claim 4, characterized in that the frame (6, 7) comprises cooling ribs (16) on its outer circumference.

13. The irradiation device according to claim 2, characterized in that the irradiation device (1) comprises a fan (15) and the cooling ribs (16) are configured such that the free cross-section (17) between the cooling ribs (16) and a housing (2) of the irradiation device (1) is optimized with respect to the air capacity of the fan (15).

14. The irradiation device according to claim 3, characterized in that the irradiation device (1) comprises a fan (15) and the cooling ribs (16) are configured such that the free cross-section (17) between the cooling ribs (16) and a housing (2) of the irradiation device (1) is optimized with respect to the air capacity of the fan (15).

15. The irradiation device according to claim 4, characterized in that the irradiation device (1) comprises a fan (15) and the cooling ribs (16) are configured such that the free cross-section (17) between the cooling ribs (16) and a housing (2) of the irradiation device (1) is optimized with respect to the air capacity of the fan (15).

16. The irradiation device according to claim 5, characterized in that the irradiation device (1) comprises a fan (15) and the cooling ribs (16) are configured such that the free cross-section (17) between the cooling ribs (16) and a housing (2) of the irradiation device (1) is optimized with respect to the air capacity of the fan (15).

* * * * *